(12) United States Patent
Doolittle, Jr.

(10) Patent No.: US 8,664,162 B2
(45) Date of Patent: Mar. 4, 2014

(54) METHOD FOR APPLICATION OF PESTICIDES AND PLANT GROWTH REGULATORS AND NUTRIENTS TO PLANTS

(75) Inventor: Glayne D. Doolittle, Jr., Omaha, NE (US)

(73) Assignee: ArborSystems, Omaha, NE (US)

( * ) Notice: Subject to any disclaimer, the term of this patent is extended or adjusted under 35 U.S.C. 154(b) by 450 days.

(21) Appl. No.: 12/508,945

(22) Filed: Jul. 24, 2009

(65) Prior Publication Data
US 2011/0021353 A1    Jan. 27, 2011

(51) Int. Cl.
| A01N 43/00 | (2006.01) |
| A01N 43/50 | (2006.01) |
| A01N 43/40 | (2006.01) |
| A01N 3/00  | (2006.01) |
| A01N 43/90 | (2006.01) |

(52) U.S. Cl.
CPC .............. *A01N 43/50* (2013.01); *A01N 43/40* (2013.01); *A01N 43/90* (2013.01); *A01N 3/00* (2013.01)
USPC ........... 504/139; 504/134; 504/130; 504/124; 504/261

(58) Field of Classification Search
CPC ................................. A01N 43/90; A01N 3/00
USPC ................... 504/139, 130, 124, 261
See application file for complete search history.

(56) References Cited

U.S. PATENT DOCUMENTS

| 4,154,596    | A   | * | 5/1979  | George et al. ................. 504/297 |
| 6,300,348    | B1  |   | 10/2001 | Sirinyan et al. |
| 2002/0103233 | A1  | * | 8/2002  | Arther ........................... 514/341 |
| 2002/0193352 | A1  | * | 12/2002 | Erdelen et al. ................. 514/114 |
| 2003/0053955 | A1  | * | 3/2003  | Taylor .............................. 424/45 |
| 2005/0158355 | A1  |   | 7/2005  | Yamashita |
| 2006/0258576 | A1  |   | 11/2006 | Immonen et al. |
| 2008/0072640 | A1  |   | 3/2008  | Fersch et al. |

FOREIGN PATENT DOCUMENTS

WO    WO2005/023861    3/2005

* cited by examiner

*Primary Examiner* — Rebecca Prouty
*Assistant Examiner* — Danielle Sullivan
(74) *Attorney, Agent, or Firm* — Fox Rothschild LLP

(57) ABSTRACT

The present invention provides methods for applying active ingredients including pesticides, plant growth regulators and plant nutrients to plants by applying formulations comprising the active ingredients and a solvent to the soil around a plant.

11 Claims, No Drawings

METHOD FOR APPLICATION OF PESTICIDES AND PLANT GROWTH REGULATORS AND NUTRIENTS TO PLANTS

BACKGROUND OF THE INVENTION

Systemic pesticides are pesticides that are absorbed by plant tissue and distributed throughout the plant by its vascular system. Systemic pesticides are widely used to regulate plant growth and to protect lawns, shrubs, foliage plants, and trees from diseases and from chewing and sucking pests such as aphids, whiteflies, mealybugs and soft scales. For example, pests ingest or come into contact with an insecticide and are eliminated when the pests feed on a treated plant.

Various methods are available for the application of systemic pesticides to plants. Spray application to foliage has been widely used, but has certain disadvantages, including weather dependence, short duration of control, and spray drift to the surrounding environment and the applicator.

Systemic pesticides may also be applied to soil by drenching or injection methods. However, many active ingredients used as pesticides, particularly those developed over the last twenty years, are sparingly soluble or insoluble in water. These active ingredients may be formulated for soil application as solid formulations such as wettable powders or wettable dispersible granules, or as aqueous suspensions or emulsion concentrates. Generally, the active ingredient is present as relatively large particles, or particles that tend to settle out or segregate upon dilution with water. After soil application of these formulations by drenching, broadcast spray, or injection, the uptake and distribution of the active ingredient throughout the plant may require several weeks or months. The soil application methods thus require treatment of the plants in advance of an expected pest infestation. Soil applications are generally therefore not useful for rescue treatments.

Other application methods for insoluble or sparingly soluble pesticides include trunk injections and trunk implants. These methods result in more rapid uptake and distribution of the active ingredient than soil applications, but require puncturing the trunk, which causes a wound to the plant and may cause long-term damage.

The present invention provides a method for application of a pesticide or other active ingredient to a plant that results in rapid uptake and distribution of the pesticide or other active ingredient without injury to the plant.

SUMMARY OF THE INVENTION

The present invention provides methods for applying active ingredients including pesticides, plant growth regulators, and plant nutrients to plants. The methods comprise applying a formulation comprising one or more of the active ingredients and a non-aqueous solvent to the soil around a plant. The methods of the present invention provide rapid uptake and distribution of the active ingredient through the plant.

In another embodiment, the present invention provides an article of manufacture comprising: a formulation comprising one or more of a pesticide, plant growth regulator and a plant nutrient and a non-aqueous solvent; and packaging material comprising a label with directions to apply the formulation to the soil around a plant in need of treatment with a pesticide, plant growth regulator, or plant nutrient.

DETAILED DESCRIPTION OF THE INVENTION

The present invention provides a method for applying a pesticide to a plant comprising applying a formulation comprising a pesticide and a non-aqueous solvent to the soil around the plant.

In another embodiment, the present invention provides a method for applying a plant growth regulator to a plant comprising applying a formulation comprising a plant growth regulator and a non-aqueous solvent to the soil around the plant.

In another embodiment, the present invention provides a method for applying a plant nutrient to a plant comprising applying a formulation comprising a plant nutrient and a non-aqueous solvent to the soil around the plant.

In another embodiment, the present invention provides a method for protecting a plant from insects comprising applying a formulation comprising an insecticide and a non-aqueous solvent to the soil around a plant.

It has been discovered in accordance with the present invention that soil application of a formulation comprising an active ingredient and a non-aqueous solvent results in rapid uptake and distribution through the plant of the active ingredient. The methods of the present invention are thus useful for the systemic delivery of active ingredients including pesticides, plant growth regulators, and plant nutrients to plants.

Pesticides that may be used in the methods of the present invention are active ingredients that are used to protect plants from pests and include, for example, insecticides, fungicides, bactericides, and nematicides. Preferred insecticides include neonicotinoid-based compounds, GABA antagonists, macrocyclic lactones, pyrethroids, carbamates and organophosphates. Neonicotinoid-based compounds include clothianidin, acetamiprid, dinotefuran, imidacloprid, thiamethoxam, nithiazine, nitenpyram, acetamiprid, and thiacloprid. Imidacloprid is particularly preferred. GABA antagonists include acetoprole, endosulfan, ethiprole, fipronil and vaniliprole. Macrocyclic lactones include abamectin, doramectin, emamectin, eprinomectin, ivermectin, milbemectin, lepimectin, moxidectin, selamectin, spinetoram, and spinusad. Pyrethroids include allethrin, tetramethrin, resmethrin, phenothrin, furamethrin, permethrin, cypermethrin, deltamethrin, cyhalothrin, cyfluthrin, fenpropathrin, tralomethrin, cycloprothrin, flucythrinate, fluvalinate, acrinathrin, tefluthrin, bifenthrin, empenthrin, beta-cyfluthrin, cypermethrin, fenvalerate, esfenvalerate, flubrocythrinate, metofluthrin, profluthrin, dimefluthrin, flubrocythrinate, silafluofen, pyrethrum extract, etofenprox and halfenprox. Carbamates include ethiofencarb, bendiocarb, pirimicarb, carbosulfan, benfuracarb, methomyl, oxamyl, aldicarb, thiodicarb, alanycarb, carbofuran, methiocarb, fenothiocarb, formetanate, xylylmethylcarbarnate, propoxur, isoprocarb and furathiocarb. Organophosphates include disulfoton, phorate, dimethoate, ciodrin, dichlorvos, dioxathion, ruelene, carbophenothion, supona, TEPP, EPN, HETP, parathion, malathion, ronnel, coumaphos, diazinon, trichlorfon, paraoxon, potasan, dimefox, mipafox, schradan, sevin, chlorpyrifos, acephate and dimeton. Another preferred pesticide is spirotetramat.

Fungicides and bactericides include acylalanines, benzimidazoles, benzothiazoles, oxanthins, organophosphates, pyrimidines, triazoles, thiaxoles, and antibiotic fungicides. Nematicides include carbamates, organophosphates, and antibiotic nematicides.

Plant grown regulators include antiauxins, auxins, cytokinins, defoliants, ethylene inhibitors, ethylene releasers, gibberellins, gibberellin inhibitors, growth inhibitors and growth retardants. Plant nutrients include naturally occurring or synthetic compounds containing one or more of nitrogen, potassium, phosphorus, calcium, magnesium, iron, zinc, boron and manganese.

The pesticide formulations used in accordance with the present invention may comprise one pesticide or a combination of pesticides, or a combination of pesticides and at least one of a plant growth regulator and a plant nutrient.

The plant growth regulator formulations may comprise one plant growth regulator or a combination of plant growth regulators, or a combination of plant growth regulators and at least one of a pesticide and a plant nutrient.

The plant nutrient formulations may comprise one plant nutrient or a combination of plant nutrients, or a combination of plant nutrients and at least one of a pesticide and a plant growth regulator.

It has been discovered in accordance with the present invention that active ingredients that are not generally considered to be amenable to systemic delivery or that are absorbed and/or delivered slowly within a plant are surprisingly effective in the present methods. In particular, pesticides that have low solubility in water and translocate in plants slowly when applied to soil or roots in aqueous suspensions are particularly useful in the formulations used in the methods of the invention. Accordingly the pesticides, plant growth regulators and plant nutrients in the formulations of the present invention preferably have a solubility in water of less than 5.0 g/L (5000 ppm) at 20° C., and more preferably less than 2.0 g/L (2000 ppm) at 20° C., and most preferably less than 1.0 g/L (1000 ppm) at 20° C. Solubility of pesticides, plant growth regulators and plant nutrients can be determined by methods known to those of ordinary skill in the art.

The present methods result in rapid translocation of the active ingredient to plant tissues such as leaves, and thus are useful not only to prevent an infestation, but also to treat an existing pest infestation.

Preferred pesticides include imidacloprid, spirotetramat, dinotefuran, abamectin, bifenthrin, permethrin, and emamectin benzoate.

Solvents useful in the formulation of the present invention are non-phytotoxic and include for example, alcohols, esters, glycols, glycol esters, and the like. Preferred solvents are alcohols.

Alcohols that may be used in the formulations of the present invention include methanol, ethanol, n-propanol, isopropanol, n-butanol, isobutanol, amyl alcohol, methyl amyl alcohol, cyclohexanol, 2-ethylhexanol, furfuryl alcohol, tetrahydrofurfuryl alcohol and d-limonene. Esters that may be used include ethyl lactate. Glycols and glycol esters that may be used in the formulations of the present invention include monoethylene glycol, diethylene glycol, propylene glycol or the methyl, ethyl, n-propyl, n-butyl or t-butyl ethers thereof, dipropylene glycol or the methyl, ethyl, n-propyl, n-butyl or t-butyl ethers thereof, tripropylene glycol, or the methyl, ethyl, n-propyl, n-butyl or t-butyl ethers thereof, 1,3-butanediol, 1,4-butanediol, 2-methyl-1,3-propanediol, 2,2-dimethyl-1,3-propanediol, 2-methyl-1,3-pentanediol, 2-methyl-2,4-pentanediol, 2-methyl-1,3-propanediol and 1,4-butanediol. Blends of various solvents may also be used. A preferred solvent is tetrahydrofurfuryl alcohol (THFA). Another preferred solvent is ethyl lactate.

The formulations may be prepared by combining and mixing the pesticide or plant growth regulator or plant nutrient and the solvent. Preferred formulations comprise from 0.1% to 50% by weight of at least one pesticide, plant growth regulator, or plant nutrient or combinations thereof and from 50% to 99.9% by weight of at least one non-aqueous solvent. More preferably, the formulations contain from 1.0% to 10% by weight of at least one pesticide, plant growth regulator, or plant nutrient or combinations thereof, and from 90% to 99% by weight of at least one non-aqueous solvent. A preferred formulation comprises from 1.0% to 10% by weight of imidacloprid and from 90% to 99% by weight of a non-aqueous solvent. Another preferred formulation comprises from 1.0% to 10% by weight of imidacloprid and from 90% to 99% of THFA. A particularly preferred formulation comprises 5.0% by weight of imidacloprid and 95.0% by weight of THFA. The formulations may optionally further include additional inert ingredients.

The formulations of the invention are applied to the soil around the base of a plant. Methods of soil application of systemic pesticides, plant growth regulators, and plant nutrients are known in the art. The formulation is preferably poured onto the soil immediately adjacent to the plant's trunk or stem, or to the nearby soil where the roots occur. The soil may then be watered to move the active ingredient into the soil. In another embodiment, the formulation is mixed with water before pouring onto the soil. The formulation may also be applied by a soil injection method. Soil injection methods are known in the art. Low volume soil injections may be made using specialized commercially available injectors to inject the formulation into the soil. Injection holes may be evenly spaced around the base of the trunk or stem, or spaced in a grid pattern or concentric circle pattern extending to the drip line of the plant. High-volume soil injections may be used, for example, if the formulation is mixed with water before application. High volume injection may be made using hydraulic sprayers with soil injector nozzles around the base of the trunk or stem, or in the grid or circular patterns described above. One of ordinary skill in the art can determine an appropriate number of injection holes, pattern of injection, and volume of injection with reference to the type and size of plant being treated.

One of ordinary skill in the art can determine the amount of active ingredient, the volume of formulation, and the amount of water, depending upon the particular active ingredient, the type of plant, the size of the plant, its root zone, and its trunk diameter, the type of soil, and the environment of the plant, e.g. nursery, landscape or forest.

The method of the present invention may be used for systemic delivery of a pesticide, plant growth regulator, or plant nutrient to any type of plant, including trees, shrubs, flowering plants, foliage plants, house plants, groundcover and grass.

Systemic delivery may be assessed by determining the presence of the pesticide, plant growth regulator, or plant nutrient in plant tissues such as leaves. The presence of the active ingredient may be assessed by a quantitative measurement, for example, by gas chromatography, high performance liquid chromatography, or an enzyme-linked immunosorbent assay. The systemic delivery of the active ingredient may also be assessed qualitatively, for example, by visual inspection of the effect of the delivery. For example, systemic delivery of a pesticide may be confirmed by observation of the reduction or elimination of pests.

A preferred embodiment of the present invention is a method of applying imidacloprid to a plant comprising applying a formulation comprising imidacloprid and a non-aqueous solvent to the soil around the plant. In a preferred embodiment, the non-aqueous solvent is THFA. In another preferred embodiment, the formulation comprises 5% by weight of imidacloprid and 95% by weight of THFA. The plant is preferably a woody-stemmed plant. The plant is more preferably a tree. In another preferred embodiment, the plant is a flowering plant, shrub, or house plant. In another embodiment, the method further comprises watering the soil around the plant after the formulation is applied. In another preferred embodiment, the formulation is combined with water before application to the soil.

Imidacloprid is useful for the control of insects including adelgids, flatheaded borers, aphids, elm leaf beetles, black vine weevil, eucalyptus longhorned borer, japanese beetles, lacebugs, leafhoppers, leafminers, mealybugs, sawfly larvae, pine ark beetles, pine tip moth larvae, psyllids, royal palm bugs, soft scale insects, and whiteflies, and for the suppression of thrips and armored scales. Accordingly, the method of applying imidacloprid is useful to prevent, control or suppress infestation by these insects.

In another embodiment, the present invention provides an article of manufacture comprising a formulation of the present invention and packaging material comprising a label with directions to apply the formulation to the soil around a plant in need of treatment with a pesticide, plant growth regulator, or plant nutrient.

In a preferred embodiment, the article of manufacture comprises a formulation comprising a pesticide and a non-aqueous solvent, and packaging comprising a label with directions to apply the formulation to the soil around a plant in need of treatment with a pesticide. In a preferred embodiment, the pesticide is an insecticide. In a particularly preferred embodiment, the formulation in the article of manufacture comprises 5% by weight of imidacloprid and 95% by weight of THFA.

The following examples serve to further illustrate the present invention.

Example 1

Application of Insecticide to Aspen Tree

Visual inspection of an aspen tree having a two inch diameter base revealed infestation with a very heavy population of aphids, and leaves shiny with honeydew produced by the aphids. The tree had not previously been treated with any pesticide. About 4 to 5 ml of a formulation containing 5% imidacloprid and 95% tetrahydrofurfuryl alcohol (THFA) was poured onto the soil around the base and then watered in.

Visual observation of the treated tree after five days indicated a complete absence of aphids, and leaves that were not shiny. One month later, no aphids were observed on the treated tree, and an untreated tree about 75 feet away exhibited aphid activity.

Leaves obtained from the treated and untreated trees 100 days after treatment were analyzed for imidacloprid by enzyme-linked immunosorbent assay (ELISA). Briefly, leaves were dried completely and leaf blade material was separated from stems and petioles. The leaf blade material was ground to a fine powder, and about 5 grams of the material placed in a vial. A measured amount of methanol was added so that the leaf material was covered and 1 to 2 ml of methanol was beyond the leaf material, for a total of 10 to 20 ml of methanol. The vials were mixed well at least twice a day for at least 48 hours. After at least 48 hours, 10 microliters of the liquid was transferred to a smaller vial, and 1.5 ml distilled water added, and the vials were mixed well. ELISA was performed using the Envirologix™ QuantiPlate Kit for Imidacloprid (EP 006). The following results were obtained.

| Sample | Leaf tissue dry weight (g) | Methanol added (ml) | Water (ml) | ELISA well number | ELISA ppb before calculations | Rough ELISA ppb | Corrected imidacloprid ppb** |
|---|---|---|---|---|---|---|---|
| Untreated 1 | 3 | 12 | 1 | A9 | 3.3* | 1667 | 0 |
| Untreated 2 | 3 | 12 | 1 | A10 | 3.4* | 1717 | 0 |
| Treated 1 | 3 | 12 | 1 | A11 | 37.7 | 19039 | 17,300 |
| Treated 2 | 3 | 12 | 1 | A12 | 36.3 | 18332 | 16,640 |

*This is small enough to be "background noise" in the analysis because of reactions with chemicals in the leaf tissue.
**After assuming a background noise is present and subtracting the average values of the untreated trees.

The average concentration of imidacloprid in leaves from the treated tree was 16,970 ppb; imidacloprid was not detectable in leaves from the untreated tree after correction for background.

This experiment demonstrates that application of a formulation of the present invention to the soil around a tree resulted in systemic delivery of effective concentrations of insecticide to leaves of the tree in five days. In contrast, when aqueous suspensions of imidacloprid are applied to soil, systemic activity is not expected for 60 days or longer. (Label for Merit® 2F Insecticide, Bayer Environmental Science, EPA Reg. No. 432-1312.)

Example 2

Application of Insecticide to Phylodendrons

Five ml of a formulation of 5% imidacloprid and 95% THFA was applied to the soil of each of two 4-inch diameter pots of phylodendrons. An equal number of control plants received no insecticide treatment. All of the plants were watered and kept in the same area. On the tenth day after treatment, leaves from treated and control plants were collected and tested for imidacloprid by ELISA as described in Example 1. The following results were obtained.

| Sample | Leaf tissue dry weight (g) | Methanol added (ml) | Water (ml) | ELISA well number | ELISA ppb before calculations | Rough ELISA ppb | Corrected imidacloprid ppb** |
|---|---|---|---|---|---|---|---|
| Untreated 1 | 0.7 | 5 | 1 | A9 | 0.4* | 329 | 0 |
| Untreated 2 | 0.7 | 5 | 1 | A10 | 0.4* | 329 | 0 |
| Treated 1 | 0.7 | 5 | 1 | A11 | 94.8 | 77,966 | 77,637 |
| Treated 2 | 0.7 | 5 | 1 | A12 | 81.0 | 66,617 | 66,288 |

*This is small enough to be "background noise" in the analysis because of reactions with chemicals in the leaf tissue.
**After assuming a background noise is present and subtracting the average values of the untreated trees.

The average concentration of imidacloprid in the leaves of the treated plants was 72,000 ppb imidacloprid. Imidacloprid was not detectable in leaves from the untreated plants after correction for background.

This experiment demonstrates that imidacloprid in an alcohol formulation applied to the soil was effectively taken up by the plant's roots and translocated to the leaves. Further, absorption by the roots and translocation to the leaves occurred in 10 days or less, while currently available imidacloprid suspension products for soil application are expected to require 60 days or more for translocation to leaves.

I claim:

1. A method for protecting the leaves of a plant from insects comprising applying a formulation comprising imidacloprid and tetrahydrofurfuryl alcohol to the soil around a plant in which the leaves are in need of protection from insects, whereby the insecticide is systemically delivered to the plant and the leaves are protected from insects.

2. The method of claim 1 wherein the formulation is applied by pouring onto the soil.

3. The method of claim 1 wherein the formulation is applied by injection into the soil.

4. The method of claim 1 wherein the formulation comprises 5% imidacloprid and 95% tetrahydrofurfuryl alcohol.

5. The method of claim 1 further comprising watering the soil around the plant after applying the formulation.

6. The method of claim 1 wherein the formulation is mixed with water before application to the soil.

7. The method of claim 1 wherein the plant is a woody-stemmed plant.

8. The method of claim 1 wherein the plant is a tree.

9. The method of claim 1 wherein the plant is a flowering plant, a house plant, or a shrub.

10. The method of claim 1 wherein the formulation is a liquid formulation.

11. The method of claim 1 wherein the formulation comprises from 50% to 99.9% by weight of tetrahydrofurfuryl alcohol.

* * * * *